United States Patent
MacKay et al.

(10) Patent No.: US 10,215,701 B2
(45) Date of Patent: Feb. 26, 2019

(54) METHOD OF ASSESSING CHEMICALS IN PRODUCED FLUIDS

(71) Applicant: LUX ASSURE LIMITED, Edinburgh (GB)

(72) Inventors: Fiona MacKay, Edinburgh (GB); Emma Perfect, Edinburgh (GB); Catherine Rowley-Williams, Linlithgow (GB); Anne-Marie Fuller, Edinburgh (GB)

(73) Assignee: Lux Assure Limited, Edinburgh (GB)

( * ) Notice: Subject to any disclaimer, the term of this patent is extended or adjusted under 35 U.S.C. 154(b) by 79 days.

(21) Appl. No.: 15/135,223

(22) Filed: Apr. 21, 2016

(65) Prior Publication Data

US 2016/0238531 A1    Aug. 18, 2016

Related U.S. Application Data

(62) Division of application No. 13/700,235, filed as application No. PCT/GB2011/000823 on May 27, 2011, now Pat. No. 9,341,571.

(51) Int. Cl.

| | |
|---|---|
| *G01N 21/33* | (2006.01) |
| *G01N 21/59* | (2006.01) |
| *G01N 21/77* | (2006.01) |
| *G01N 21/78* | (2006.01) |
| *G01N 21/85* | (2006.01) |
| *G01N 21/3577* | (2014.01) |
| *G01N 21/64* | (2006.01) |
| *G01N 21/65* | (2006.01) |
| *G01N 21/76* | (2006.01) |
| *G01N 21/75* | (2006.01) |

(52) U.S. Cl.
CPC ......... *G01N 21/6428* (2013.01); *G01N 21/33* (2013.01); *G01N 21/3577* (2013.01); *G01N 21/59* (2013.01); *G01N 21/65* (2013.01); *G01N 21/76* (2013.01); *G01N 21/77* (2013.01); *G01N 21/78* (2013.01); *G01N 21/85* (2013.01); *G01N 2021/755* (2013.01); *G01N 2021/7786* (2013.01); *G01N 2333/904* (2013.01); *Y10T 436/203332* (2015.01)

(58) Field of Classification Search
CPC ........... G01N 21/3577; G01N 21/6428; G01N 21/77; G01N 21/78; G01N 21/85
See application file for complete search history.

(56) References Cited

U.S. PATENT DOCUMENTS 5,239,860 A    8/1993   Harris

FOREIGN PATENT DOCUMENTS

WO    20100007390 A2    1/2010

OTHER PUBLICATIONS

Yun-Pie Wu et al (Determination of ethylene glycol using periodate oxidation and liquid chromatography. Analyst, 1985, 110, 1073-1076 (Year: 1985).*
Rajagopal G, et al A new method for estimation of ethylene glycol in biological material Anal. Biochem., 1975, 65, 132 (Year: 1975).*
Williams, Robert H. et al., "Simultaneous Detection and Quantitation of Diethylene Glycol, Ethylene Glycol, and the Toxic Alcohols in Serum using Capillary Column Gas Chromatography", Journal of Analytical Toxicology, vol. 24, p. 621-626, Oct. 2000, Oxford University Press, Oxford, UK.
Anthon, Gordon E. et al., "Comparison of Three Colorimetric Reagents in the Determination of Methanol with Alcohol Oxidase. Application to the Assay of Pectin Methylesterase", Journal of Agricultrual and Food Chemistry, vol. 52, pp. 3749-3753, May 12, 2004, American Chemical Society, Washington, D.C.
Mangos, Thomas J. et al., "A Spectrophotometric Assay for the Enzymatic Demethoxylation of Pectins and the Determination of Pectinesterase Activity", Analytical Biochemistry, vol. 244, pp. 357-366, 1997, Elsevier Inc., Waltham, MA.
Wojciechowski, Cheryl L. et al., "A Continuous Fluorometric Assay for Pectin Methylesterase", Analytical Biochemistry, vol. 237, pp. 103-108, 1996, Elsevier Inc., Waltham, MA.
Sheehan et al. "A new alcohol dehydrogenase, reactive towards methanol, from Bacillus stearothermophilus" Biochem. J. (1988) 252, 661-666.
Kraut et al. "Toxic Alcohol Ingestions: Clinical Features, Diagnosis, and Management" Clin J Am Soc Nephrol 2008 3: 208-225.
Worthington Biochemical Corporation (introduction to Enzymes 2001).
Atkinson et al. Inhibition of alcohol dehydrogenase from yeast pyridine Biochem. J 1967 104 372-377.
DeAgulia et al. "Comparing protocols for preparation of DNA-free total yeast RNA suitable for RT-PCR" BMC Molecular Biology 2005, 6 1-6.
Men et al. "The Oxidation of Yeast Alcohol Dehydrogenase-1 by Hydrogen Peroxide in Vitro" Journal of Proteome Research 2007, 6, 216-225.

* cited by examiner

*Primary Examiner* — Kagnew H Gebreyesus
(74) *Attorney, Agent, or Firm* — Ostragner Chong Flaherty & Broitman PC

(57) ABSTRACT

A method of monitoring water-soluble treatment chemicals in a fluid that is immiscible with water and which may or may not contain some aqueous fluid, the method using at least one reagent that produces an optically detectable product, the detection step can take place without separation of the aqueous phase containing the treatment chemicals from the fluid immiscible with water.

43 Claims, 13 Drawing Sheets

METHOD OF ASSESSING CHEMICALS IN PRODUCED FLUIDS

RELATED PATENT APPLICATION

This application is a divisional of and claims priority from U.S. patent application Ser. No. 13/700,235 filed on Jun. 21, 2013, which is the U.S. national stage application under 371 of International Application No. PCT/GB2011/000823 filed on May 27, 2011.

TECHNICAL FIELD

The invention relates to a method of monitoring chemicals in fluids that are immiscible with water, that are produced by the oil and gas industry. More specifically, the invention relates to a convenient method of monitoring treatment chemicals in oil, condensate, export oil, heavy oil, hydrocarbon streams, diesel, lubricants, waxes, biofuels, biodiesels, petroleum products, other products from refining, distillation and processing of oil and gas products and also including those with small quantities of water.

BACKGROUND

Treatment chemicals, also termed chemical additives, are introduced into the fluid in the systems, following monitoring or diagnosis of a particular problem or to improve performance. The term may include polymeric scale inhibitors, phosphonate scale inhibitors, corrosion inhibitors, hydrate inhibitors (such as methanol and monoethylene glycol), wax inhibitors, anti-fouling agents, asphaltene inhibitors, hydrogen sulphide scavengers, pH stabilisers, flow additives, anti-foaming agents, ethanol, enhanced oil recovery polymers, detergents and demulsifiers. Such chemicals are commonly used in the oil and gas industry, particularly in oil and gas wells, oil and gas pipelines and petrochemical processing plants and refineries and on the forecourt of gasoline pumping stations.

Methanol is a commonly used additive. Major uses of methanol include use in antifreeze, as a solvent, direct use as fuel, a denaturant for ethanol to prevent "liquor" taxes being applied, synthesis of biodiesel and in feedstock. Methanol is particularly useful in the offshore oil and gas industries. Methanol is the most widely used hydrate inhibitor in crude oil production (hydrates are crystals of water and gas) because it is inexpensive and easy to produce.

Methanol is injected into wells to prevent plugging and freezing of gas pipeline in cold areas, which helps to avoid costly downtime due to freeze-ups of deep water well systems.

Monitoring of methanol is crucial for a number of reasons. For example, it is necessary to monitor methanol exposure in the work place for toxicity reasons. It is important to conduct environmental monitoring, for example of industrial effluents, to prevent unacceptable levels of pollution. Methanol levels must be monitored in fuels and fuel emissions, as well as in food, beverages and consumer products to prevent human exposure. Finally, it is useful to determine levels of methanol in biological samples from normal, poisoned and occupationally exposed individuals.

Within the oil and gas industry, monitoring of methanol is especially important, in order to control methanol levels. Methanol content can have an effect on hydrocarbon permit limits and bioremediation at refinery wastewater facilities. Methanol is miscible with water; in a multiphase oil, water and gas stream, the majority will get carried with the water in the system and may be disposed of to the sea or may be transported to the refinery, although some will partition to the hydrocarbon phase. When the refinery processes crude containing methanol the majority of the methanol is removed with the water and sent to the water treatment system where it can drastically upset the balance of the system leading to EPA permit excursions. This happens because the bacteria used to breakdown other components prefer the methanol instead, leaving other hydrocarbons & toxins untreated. A big enough upset can also lead to a "bug kill" which renders the treatment system useless and typically requires major remediation to get the system back in balance. Refineries will typically opt to cut runs vs. risking a permit excursion and future penalties. Methanol can also drastically lower the efficiency of the activated titanium catalyst used in gas fractionation processes. Methanol that remains in the hydrocarbon phase moves into the profitable propane stream sending it off specification and may result in costly flaring. Typically, terminals, refineries and processing facilities will opt to cut runs rather than risk a permit exclusion and future penalties. They will look to recoup these costs by discounting crudes, applying levies for the use of methanol or charging suppliers if levels go above an agreed limit. This is especially problematic when a number of systems that share the same export pipeline are started up and so use methanol at the same time, a situation that can occur during hurricane season in the Gulf of Mexico, or where multiple suppliers share a common export pipeline.

Monoethylene glycol is another commonly used additive, also known as MEG, ethylene glycol, 1,2-ethanediol or ethane-1,2-diol. Major uses of MEG include use as a coolant in engines and personal computers, as a deicer, in air conditioning systems, in plastic manufacturing particularly of polyesters and to protect groups in organic synthesis. MEG is commonly used in oil and gas facilities as a hydrate inhibitor and as a corrosion inhibitor in a cocktail of other chemicals. MEG can also be used for dehydration of natural gas streams and natural gas liquids, and is the most common and economical means of water removal.

Monitoring of MEG is important in a number of areas. Detection of poisoning with anti-freeze in serum and other bodily fluids can be done by detection of MEG. Contamination of fuel and lubricants (for example, when as little as 50 ppm MEG gets into lubricating oil systems, the mixture can polymerise into a viscous fluid plugging lines and ports and accelerating wear) can be monitored. Environmental monitoring of MEG is useful, for example there are a number of examples of contamination of water sources including rivers and streams and drinking water from run-off and storm drains from airports e.g. Albany, N.Y., Lambert field, St Louis and Anchorage, Ak. and industrial sites. Finally, MEG in glycol recycling operations can be monitored in order to regulate efficiency of recovery and collection systems.

Within the oil and gas industries, there are many situations in which it is useful to monitor MEG. Minimum inhibitory concentration (MIC) of MEG must be maintained in offshore equipment to prevent hydrate formation and corrosion. MEG may damage catalysts, so that the quality of oil being exported to processing plants and refineries is compromised. Therefore, although the MIC must be maintained, the levels must be monitored to ensure that they do not rise too high, both to prevent use of fluids containing too much MEG and to reduce any charges levied on oil and gas industry operators by refineries due to high levels of MEG. It is also useful to be able to check the efficiency of MEG regeneration and reclamation plants.

Market intelligence indicates that MEG is more expensive than methanol (also used as a hydrate inhibitor) but it can be more easily recovered and reinjected therefore reducing operational costs. MEG regeneration and reclamation systems have therefore been built. A MEG regeneration system is strictly used to remove water from the produced water/MEG mixture whereas; a MEG reclamation system will also remove various other impurities e.g. salt. MEG is also likely to become more important in the future as it is expected the number of sub-sea tie backs, which connect new discoveries to existing production facilities, will increase in areas such as Alaska, necessitating the use of more methanol and MEG. Therefore, it is considered by the industry that MEG will become a more important chemical in the future and so better detection methods will be required.

Other glycols are also used in the oil and gas industry and may require monitoring for efficiency and hazard reasons. For example, glycol enhanced water-based muds can improve injection.

Ethanol is a commonly used fuel and fuel additive, indeed this is the largest single use of ethanol. Gasoline blends consisting of a wide range of ethanol concentrations (20-100%) are used, particularly in countries such as Brazil and the United States. It is important to accurately measure the ethanol content of such mixtures. Knowledge of the gasoline:ethanol ratio can allow improvements to be made to the drivability and cold starting characteristics of internal combustion engines. Too much ethanol can damage engines so monitoring levels in fuel is important. Ethanol may also be used as a hydrate inhibitor, including as a component in industrial methylated spirits. Issues may arise if small amounts remain in the hydrocarbon stream during processing, leading to contamination of the butane stream and reduction in value of the product.

Typical methods for measuring gasoline:ethanol ratios have involved measuring intrinsic properties such as the dielectric constant, thermal conductivity, index of refraction, change in the speed of sound through the mixture and microwave absorption. These methods can often require expensive equipment or knowledge on the detailed properties of the gasoline used. Infrared spectroscopy is a possible alternative but the sensitivity of this technique can be an issue (U.S. Pat. No. 5,239,860).

In addition to there being benefits for terminals, refineries and processing facilities to monitor the levels of methanol, MEG and ethanol in hydrocarbon streams there is also a benefit in monitoring for suppliers. It can be useful for suppliers to monitor and record levels in their own product, so as to show they are meeting specifications. This in turn may help minimise restrictions. Understanding how these chemicals partition between the water and hydrocarbon phases, where hydrocarbon phases can refer to a gas phase, can also help optimise production systems as well as ensuring more accurate reporting of amounts being shipped for processing.

Corrosion inhibitors are widely used in many industries including the oil and gas and water industries. Corrosion inhibitor residuals are difficult to detect, with no 'simple' test being available, particularly for offshore use. The impact of better monitoring on regulations in the oil and gas industry would be positive as the current 'usage equals discharge' policy is unlikely to hold true since residuals are expected to be present in oil. Better monitoring will have consequences for regulations and environmental discharge. Some progress has been made in determining concentration of components e.g. using ESI-MS. However, detection of corrosion inhibitor residuals remains difficult, particularly offshore.

Gas chromatography is by far the most common method of measuring methanol concentration in the oil and gas sector. Methods include the Standard Method, ASTM D7059. The accuracy for results below 5 ppm cannot be quantified, and such tests typically take 45 minutes for one sample. The ANTEK P 1000 is a methanol specific process/on-line analyser developed by PAC (a supplier of testing and analysis equipment, http://www.paclp.com). The P 1000 Methanol Analyser combines process gas chromatography (GC) with flame ionisation detection (FID).

GC methods are also used in the detection of MEG in a number of sectors, and has been described in a number of publications (Emergency medicine for detection of toxic glycols and alcohols, Williams R H, Shah S M, Maggiore J A and Erickson T B (2000); Simultaneous detection and quantitation of diethylene glycol, ethylene glycol, and the toxic alcohols in serum using capillary column gas chromatography. Journal of analytical toxicology. 24, (7) 621-626). The presence of 5-200 ppm MEG in engine oil can be detected using the ASTM method (D4291-04 Standard Test Method for Trace Ethylene Glycol in Used Engine Oil). ASTM D4291 can be adapted for use with oil field fluids. The MEG is extracted into water and a back extraction can also be incorporated to remove residual organic components. The GC apparatus is calibrated with samples containing known amounts of MEG before running real samples. Each sample run takes 12 minutes, plus 12 minutes for water blank. Running standards used for calibration takes 2 h 48 min. Including the water extraction step, this gives a time of 3 h 20 min for running a single sample. Results show that the minimum quantifiable concentration is 0.5 ppm, and reproducibility at 25 ppm is +/−2 ppm (8%). If the samples contain more than 50 ppm MEG then they must be diluted and reanalysed. Residual MEG on the apparatus column can render further readings unusable and water blanks need to be used, which extends the duration of the assay. Such assays are not automated, as they require extraction funnels and sometimes centrifugation. They are therefore very time consuming.

GC methods are also used to monitor ethanol, for example the percentage of ethanol of the fuel ethanol that is blended into gasoline (ASTM D5501).

GC methods are not ideally suited for offshore use, because they require complex procedures requiring lab time, in-depth training of lab staff and sensitive equipment which may not be robust to offshore environment. Alternatively, samples can be shipped to shore for onshore laboratory analysis. This is costly, time-consuming and results can be delayed.

Some colourmetric methods have been used for aqueous samples (J. Agric. Food Chem. 2004, 52, 3749; Anal. Biochem. 1996, 237, 103; Anal. Biochem. 1997, 244, 357) The presence of oil in samples makes analysis significantly more difficult since the oil scatters the optical signal and may interfere with the action of the detection reagents. For instance the reagents or reaction intermediates may be denatured or may be more soluble in the non-aqueous phase and therefore be removed from the aqueous phase.

For the purposes of this patent application, the term 'fluids immiscible with water' includes oils, gas, condensate, heavy oil, export oil, hydrocarbon streams, waxes, biofuels, biodiesels, petroleum products, lubricants and products from refining, distillation and processing of oil and gas products and also including those with quantities of water, gas or both.

For the purposes of this patent application, the term 'first reagent(s) refers to chemicals or enzymes that react or interact with treatment chemical in a sample to generate a first product. This first product may be optically detectable. The term 'second reagent(s)' refers to chemicals or enzymes that react with the first product to generate a second product that is optically detectable. Preferably the first or second product is fluorgenic, or chromogenic, although may be luminescent or IR- or raman-active. More specifically, where methanol is to be detected preferably the first reagent oxidises methanol to produce formaldehyde or hydrogen peroxide as the first product, which is detected with the second reagent MBTH, Fluoral-P Amplex Redor Purpald. If the sample contains ethanol and methanol then preferably catalase is added to remove interference from ethanol. Where MEG is to be detected preferably the first reagent lead tetraacetate, periodate or periodic acid is used to oxidise the sample with the second reagents MBTH, Fluoral-P or Purpald used for detection of the formaldehyde produced. If a corrosion inhibitor is to be detected then preferably chromogenic agents that react with aromatic groups, unsaturated bonds, hydroxyls or amine groups are used preferably NanoOrange®, nile red, Laurdan, FM 4-64 and 2,6-ANS. If ethanol is to be detected, preferably the first reagent oxidises ethanol and preferably the first reagent is alcohol dehydrogenase.

For the purposes of this patent application the term reactive includes any reaction or interaction between treatment chemical and reagents which forms a different chemical or results in a detectable change in the sample.

The term 'extraction' refers to transferring the treatment chemical from a fluid that is immiscible with water to an aqueous phase. The term 'separation' means the physical separation of the two phases into separate vials.

SUMMARY

According to the invention, there is provided a method of monitoring water-soluble treatment chemicals in a fluid that is immiscible with water and which may or may not contain some aqueous fluid, the method comprising obtaining a sample of said immiscible fluid, adding water to the fluid sample to form an aqueous phase containing the treatment chemical, adding a first reagent to the fluid sample, the first reagent being reactive with the treatment chemical to produce a first product; adding a second reagent to the fluid sample, the second reagent being reactive with the first product; and detecting an optically detectable product of the reaction between the second reagent and the first product, wherein the detection step can take place without separation of the aqueous phase containing the treatment chemicals from the organic phase of the sample.

This method provides an extremely convenient method for detection of methanol, MEG, ethanol, corrosion inhibitor or other treatment chemicals in a fluid that is immiscible in water and which may or may not contain some aqueous fluid. No phase separation step is necessary in order to detect the optical signal, so that the time taken to complete an assay for one sample is dramatically reduced. Furthermore, the assay can be conducted within a single sample holder, which is advantageous over prior art methods for the purpose of off-shore use, because less expensive or complicated equipment is necessary. The method can be performed by less skilled operators, the equipment is sufficiently simple to be used for offshore use and is more reliable than prior art methods, because it has fewer steps in which operator-based error may occur.

This method can be used to detect treatment chemicals in pressurised samples by adding a single or multiphase fluid to the aqueous detection reagents. This can be done under pressure or by bubbling the entire fluid through the aqueous detection reagents. If the treatment chemical is present in the gas phase it can be extracted by bubbling the gas through the aqueous detection reagents, for instance such a method could be used to extract gaseous methanol into an aqueous solution.

Preferably, the second reagent is fluorescent, chromogenic, luminescent or IR- or Raman-active in the presence of or upon reaction with the first product. It is particularly surprising that it is possible to obtain such signals from a mixed sample, and that it is not necessary to separate the fluids first. It is also surprising the reagents work in the presence of hydrocarbon based fluids, such fluids could contain substances that denature the first or second reagents, or the reagents could prefer to reside in the hydrocarbon phase. In addition, fluids that are not immiscible in water frequently contain many substances that interfere with signal detection.

Detection of an optical signal following a one-step assay such as that of the invention is very useful within the oil and gas industry. In the prior art, it has been necessary to remove the MEG, ethanol, corrosion inhibitor or methanol that separates into the aqueous phase from the sample in order to detect such a signal and ensure the reagents work. An optical signal is easily observed and quantifiable, as the signal observed is proportional to the amount of MEG, ethanol, corrosion inhibitor or methanol present in the sample.

Preferably, the water added to the fluid sample contains the first and second reagents so that they are added to the fluid immiscible with water simultaneously. This is possible because according to the invention, no water separation step is necessary in order to detect the product of the first reaction, between first reagent and treatment chemical, or product of reaction between the second reagent and the first reaction product. By adding all of the reagents at once, the time taken to complete the assay is further reduced. The simultaneous addition of the second reagent may also help ensure that any product from the first reaction does not become solubilised into the hydrocarbon but is converted to a water soluble product that is detected in the aqueous layer.

Additional water may be added before or after the reagents are added, in order to make up the sample to a specific volume. This would be of benefit where a specific volume is required in order to ensure that measurements are reproducible between different samples or where the detection equipment needs a constant, or minimum, volume. If this is required, it may be necessary to include the step of pre-marking a container into which the sample will be placed, in order to indicate the desired volume.

The method may be used to provide a yes or no answer as to whether a treatment chemical is present, a semi-quantitative or quantitative result.

Detection reagents that have been inactivated, or do not contain a particular reagent may be used to act as a control. Preferably an active first reagent is not present but a second reagent is which allows signal that corresponds to sample background, such as colouration or presence of first reagents products, to be taken. This background signal can then be subtracted from the results generated with both reagents, thereby improving the accuracy of the result by removing background.

An aqueous or oil sample, or a number of samples, known to contain treatment chemical may be provided, or prepared by the end user. Signal from this sample acts as a control to check the method was run correctly and also acts as a calibration point to compensate for any differences in reagent activity between kits or with time. Such changes may occur if reagents' are not stable and their activity changes with time or conditions.

Extending the detection range makes the method more applicable and useful. However, absorbance readings are generally only reliable up to 2 a.u. and given that this approach does not use a separation step dilution after extraction is not possible and any dilution is limited by the volume of the vial used, which must fit within the detection equipment. Extending the range may be achieved through altering the ratio of oil sample and detection reagent with a lower volume of oil and higher volume of reagent used for higher treatment chemical concentrations. The volume of the aqueous phase can be increased by proportionally increasing all the reagents or by adding water. Preferably between 0.25 and 3 mL of oil is used for methanol, ethanol and MEG testing. Extending the range may also be achieved by diluting oil with a second clean hydrocarbon before being used, where clean means it does not contain the treatment chemical of interest. This ensures similar volumes of oil are used which may reduce variability and is of particular benefit for oil samples with very high concentrations of treatment chemical. The density of the second hydrocarbon may be matched with the sample and preferably petroleum ether, or medium weight hydrocarbons such as heptane, hexane, octane or kerosene is used. Extending the range may also be achieved by making the assay conditions less than optimal, by changing concentrations, temperature, timings, or pH, so that less product is formed or using a wavelength for detection where the products extinction coefficient is lower.

Known amounts of treatment chemical can be used as standards to create calibration curves from which the concentration of treatment chemical present in the fluid sample can be calculated. These standards can be prepared in water or in another relevant fluid and run under the same conditions as the samples. Positive and negative control samples may be used to ensure the method has been followed properly, for accuracy, and as a check of the activity of reagents, of the treatment chemical detection. The negative control may contain inactivated first and/or second reagents or only the second reagent. Additionally, the value of any optically detected background signal from the negative control could be subtracted from the optically detected value obtained from a sample of produced fluid immiscible with water being analysed.

The treatment chemical may be selected from the group consisting of polymeric scale inhibitors, phosphonate scale inhibitors, corrosion inhibitors, hydrate inhibitors (such as methanol, ethanol and monoethylene glycol), wax inhibitors, anti-fouling agents, asphaltene inhibitors, hydrogen sulphide scavengers, pH stabilisers, flow additives, antifoaming agents, ethanol, detergents and demulsifiers. Such treatment substances are commonly used in the oil and gas industry, particularly in oil and gas wells, oil and gas pipelines and petrochemical processing plants.

The treatment chemical may be MEG or methanol and the first product may be formaldehyde or hydrogen peroxide. Where the treatment chemical is methanol, the first reagent may be one of alcohol dehydrogenase, methanol dehydrogenase, alcohol oxidase, formaldehyde dismutase, persulfate, permanganate or chromate. Where the treatment chemical is monoethylene glycol, the first reagent may be one of lead tetraacetate, periodate, periodic acid, boronic acid, glycerol dehydrogenase, monoethylene glycol dehydrogenase or ruthenium complexes such as $[Ru(III)(bpy)_3]^{3+}$.

The first reagent may be an oxidising agent and the first product may be one of acetaldehyde, formaldehyde, hydrogen peroxide, oxalate or NADH. Where the first product is oxalate, the second reagent is oxalate oxidase. Where the product is NADH, it will have been converted from NAD to NADH. NADH is conveniently detectable by spectroscopy. Where the product is formaldehyde, it will be converted to a detectable product by addition of 3-methyl-2-benzothiozilinone hyrazone hydrochloride (MBTH), 4-amino-2-penten-3-one (Fluoral-P) or 4-amino-3-hydrazino-5-mercapto-1,2,4-triazole (purpald), the product will be detectable by spectroscopy.

The first reagent may be one of alcohol dehydrogenase, methanol dehydrogenase, alcohol oxidase, formaldehyde dismutase, persulfate, permanganate or chromate. These reagents will be used where the treatment chemical is methanol. Where the treatment chemical is monoethylene glycol, the first reagent may be selected from periodate, periodic acid, lead tetraacetate, monoethylene glycol dehydrogenase, boronic acid, glycerol dehydrogenase, or ruthenium complexes such as $[Ru(III)(bpy)_3]^{3+}$.

The second reagent may be one of 3-methyl-2-benzothiozilinone hyrazone hydrochloride (MBTH), 4-amino-2-penten-3-one (Fluoral-P), 4-amino-3-hydrazino-5-mercapto-1,2,4-triazole (purpald), NAD, Fuschin dye, formadehyde dehydrogenase, horse radish peroxidase, 10-Acetyl-3,7-dihydroxyphenoxazine (Amplex Red®), Amplex Ultrared, 2,2'-azino-bis(3-ethylbenzthiazoline-6-sulfonic acid (ABTS), 3,3',5,5'-tetramethylbenzidine (TMB), o-phenylendiamine dihydrochloride (OPD). 2,4-Dinitrophenylhydrazine (DNPH, Brady's reagent), phenazine methosulphate-3-(4,5-dimethylthiazol-2-yl)-2,5-diphenyl tetrazolim bromide (PMS-MTT), reversible binding with fluorescent dyes, gallic acid, thiamine, nitrophenol and umbelliferone oxyamines or gallic acid in alkaline solution or phloroglucinol.

The treatment chemical may be a corrosion inhibitor. In this case, the first reagent reacts in a manner that includes but is not limited to a change in hydrogen bonding that lead to changes in fluorescence response, is reactive with aromatic groups, hydrophobic environment, unsaturated bonds, and amine groups. This reaction, or the products of the reaction, may be directly detectable.

Optional steps which may enhance the efficiency of the reaction may include mixing, vortexing, heating, shaking, sonicating, inverting, filtering or centrifuging the sample and reagents. This may help to improve separation of aqueous phase or to distribute the reagents and treatment chemical throughout the aqueous phase. The sample is preferably heated to elevated temperatures above ambient.

There may be chemicals present in the sample that could interfere with reactions. In such a case it would be beneficial to incorporate a clean up step to remove such interferences. This would help to improve the accuracy of the assay for quantification purposes. A clean up step may be physical, such as centrifuging the samples, or addition of a chemical to minimise signal from the interference. Preferably desalting columns may be used and the sample passed through a desalting column to remove salts. Preferably ethylenediaminetetraacetic acid (EDTA) or other chelator, is added to chelate interfering entities. Where ethanol is present in methanol-containing samples, and where a methanol-specific signal is desired, the interfering signal generated from reaction between ethanol and alcohol oxidase can be minimised by first adding to the sample enzymes or chemicals which react specifically with ethanol preventing its reaction with alcohol oxidase. These include, but are not limited to alcohol dehydrogenase (ADH), used together with nicotinamide adenine dinucleotide (NAD), which prefers ethanol to methanol, use of an iodine solution and sodium hydroxide solution which in the presence of ethanol forms triiodomethane or catalase which breaks down hydrogen peroxide. Preferably excess enzymes or chemicals are used to minimise the signal from ethanol. Preferably where hydrogen peroxide is present in samples undergoing tests for methanol catalase is added to minimise interference.

Different hydrocarbons may have different extraction efficiencies with the aqueous reagents. This may be influenced by characteristics such as the density of the hydrocarbon, its water content, or the presence of treatment chemicals. A calibration constant may be applied to account for these different extraction efficiencies.

Preferably, the optical signal will be detected using fluorescence, chemiluminescence, colourimetry or UV-visible, IR or Raman spectroscopy or by eye all of which are simple, inexpensive and robust and therefore ideal for use off-shore. The analysis can be carried out so that the beam of light passes through the aqueous layer only, thereby avoiding interference from aqueous immiscible fluids which may be coloured, fluorescent or containing other interfering components. The signal may be analysed, for example to compare it to a set of calibrated results in order to determine the concentration of MEG or methanol in the sample, by feeding the detected signal from the spectrometer detector into a computer. Where aqueous fluid is already present in a sample that contains fluid that is immiscible with water there may be a mark on the vial to be used that guides the addition of the correct volume of reagents and water to avoid dilution effects.

The signal may be detected using fluorescence detector, luminescence detector, Raman detector, optical microscope, CCD camera, photographic film, fibre-optic device, photometric detector, MEMS device, single photon detector, spectrophotometer, chromatography system or by eye.

Preferably, the method is automated. As such, any potential for operator-based error or variation between operators would be reduced greatly and the time taken to complete a single assay reduced.

BRIEF DESCRIPTION OF THE DRAWINGS

The invention will now be described with reference to the following figures, in which.

DESCRIPTION OF PREFERRED EMBODIMENTS

Experiment 1: MEG in Crude Oil

An experiment was conducted in order to investigate the suitability of the MEG assay to the oil and gas industries. Firstly, to determine whether the reagents would be able to function in the presence of crude oil, which contains numerous compounds that may interfere. Secondly, to assess whether it was possible to detect a signal from the sample without first separating the oil and aqueous phase.

Various concentrations of MEG were spiked into black crude oil. A stock solution of 0.1% (1,000 ppm) MEG was prepared and then serial diluted to create a range of MEG concentrations.

The assay was conducted by adding sodium periodate in buffer (50 mM) to oil samples. The samples were mixed by rotating for 15 min, then an equivalent of Fluoral-P was added. After heating for 30 min the samples were centrifuged and then the absorbance recorded. Four concentrations of MEG (20, 10, 5 and 0 ppm) were run in quadruplicate.

Figure 1:
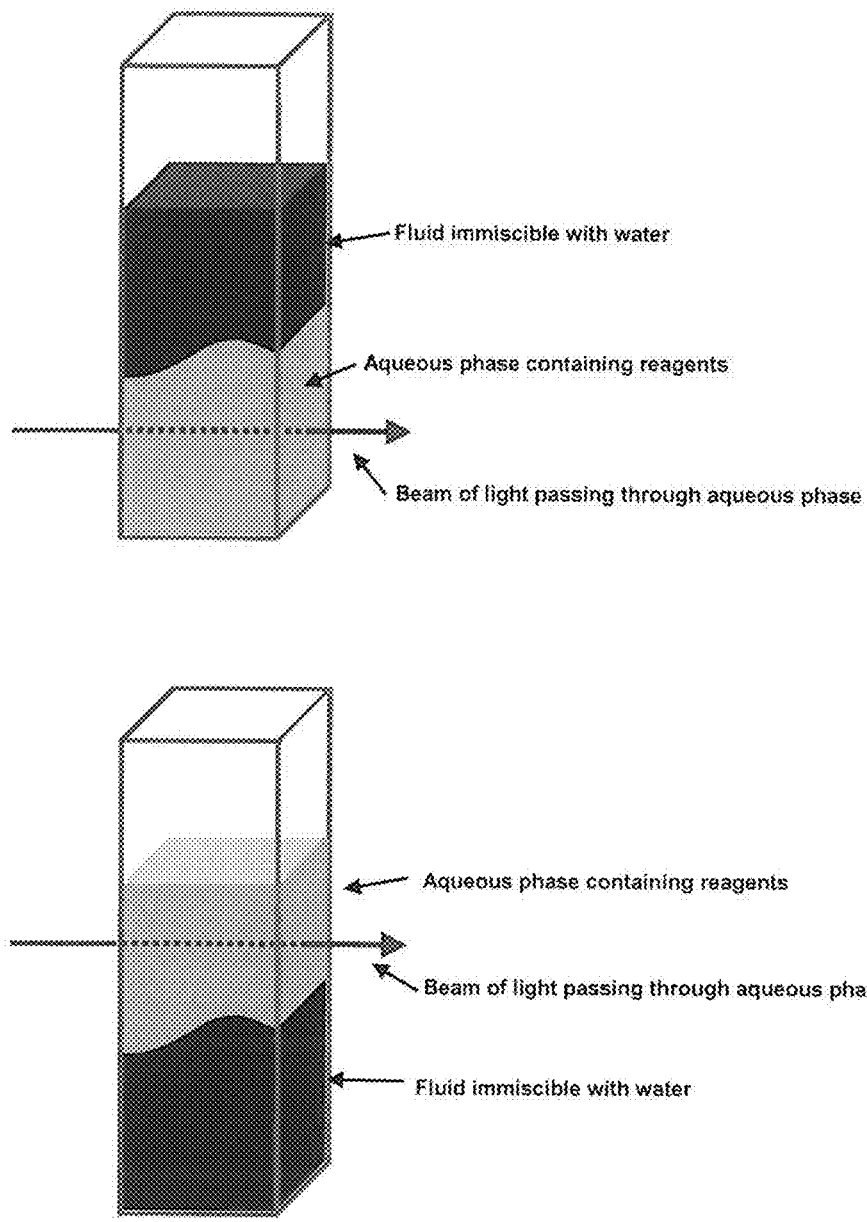
FIG. 1 is a diagram illustrating the separation of the aqueous and water-immiscible phases in a sample holder, with a beam of light that can be used for detection passing through the aqueous phase.
Figure 2:
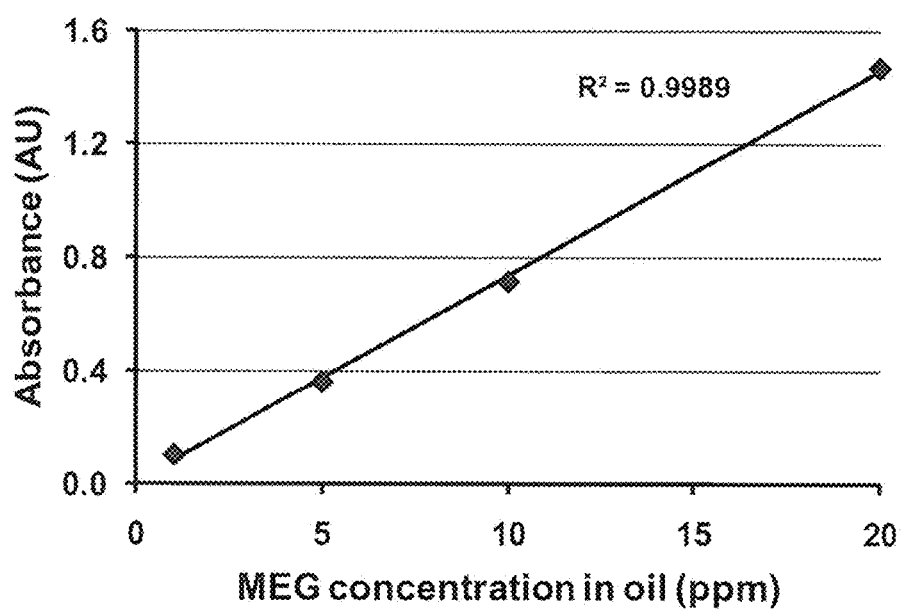
FIG. 2 is a graph showing the signal generated from a range of concentrations of MEG in oil, data is the average of triplicate samples and error bars (where visible) represent standard deviation.

The results clearly show an increasing signal with increasing MEG concentration (FIG. 2). The data was fitted linearly with $R^2=0.9989$. The errors represent standard deviation between quadruplicate samples and are very small indicating the assay repeatability is extremely good.

In the field, a sample may be taken from an oil or gas producing, refining, distilling or processing plant; from oil fields; from fuels; from produced or overboard fluids or from hydrocarbon streams. The samples may be taken in-line, at-line, on-line or offline. The reagents may be added to the sample by hand, or by automatic injector. The latter would offer the possibility for automating the system, which would make it especially reliable and high-throughput.

Experiment 2: Reproducibility and Accuracy of MEG Assay

Figure 3:
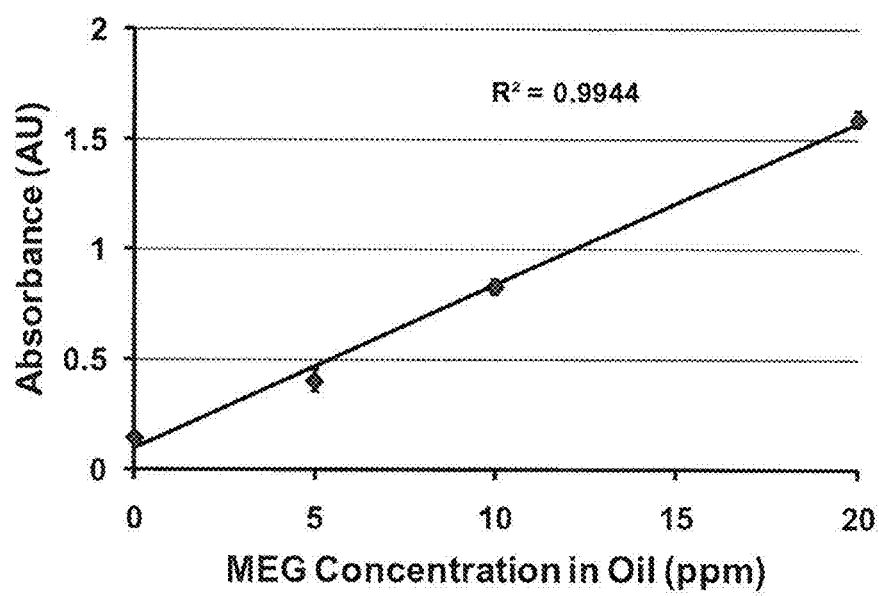
FIG. 3 shows the reproducibility between samples of MEG in oil run at different times, results are the average of three assay runs and error bars represent standard deviation.

To check the reproducibility of the assay, oil samples containing 20, 10, 5 and 0 ppm MEG were analysed on different days. The data from the three runs was averaged and is displayed with standard deviation error bars in FIG. 3. The data was fitted linearly with $R^2=0.9944$.

Figure 4:
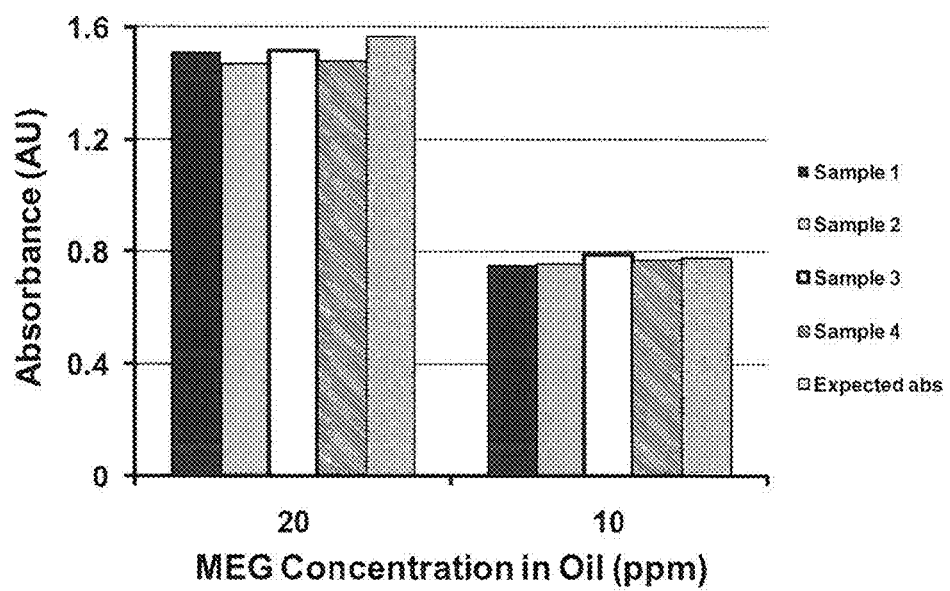
FIG. 4 is a graph showing the reproducibility between four replicate samples each spiked separately, this was carried out at two different MEG concentrations (20 and 10 ppm). A comparison of the results with the expected absorbance based on a linear fit of aqueous controls is also shown.

The agreement between samples spiked separately was also investigated to ensure the spiking method was reproducible. The signal generated by four samples, at both MEG concentrations (20 and 10 ppm), were very similar indicating the spiking method is reproducible and giving further evidence that the assay is repeatable (FIG. 4).

The accuracy of the method was determined by comparing the signal generated from oil samples containing MEG to samples which were run in the absence of oil i.e. aqueous only samples. The data from the aqueous samples was fitted linearly and the results compared with those for the oil samples (FIG. 4). The comparison between the aqueous controls and the oil samples was very good with very similar absorbances produced for both sample types.

This experiment demonstrates that in an organic fluid environment that might be expected to contain impurities which would interfere with the chemical reactions involved in detecting MEG at such low concentrations the assay still functions well.

In the field, a sample may be taken from an oil or gas producing, refining, distilling or processing plant; from oil fields; from fuels; from produced or overboard fluids or from hydrocarbon streams. The samples may be taken in-line, at-line, on-line or offline. The reagents may be added to the sample by hand, or by automatic injector. The latter would offer the possibility for automating the system, which would make it especially reliable and high-throughput.

Experiment 3: MEG in Condensate

A further experiment was conducted in order to investigate the suitability of the assay to the oil and gas industries and in particular whether the assay was compatible in a range of oil and gas fluids. Unlike experiments such as Experiment 1 which used crude oil, condensate was tested here to determine if the method worked with this different fluid.

Figure 5:
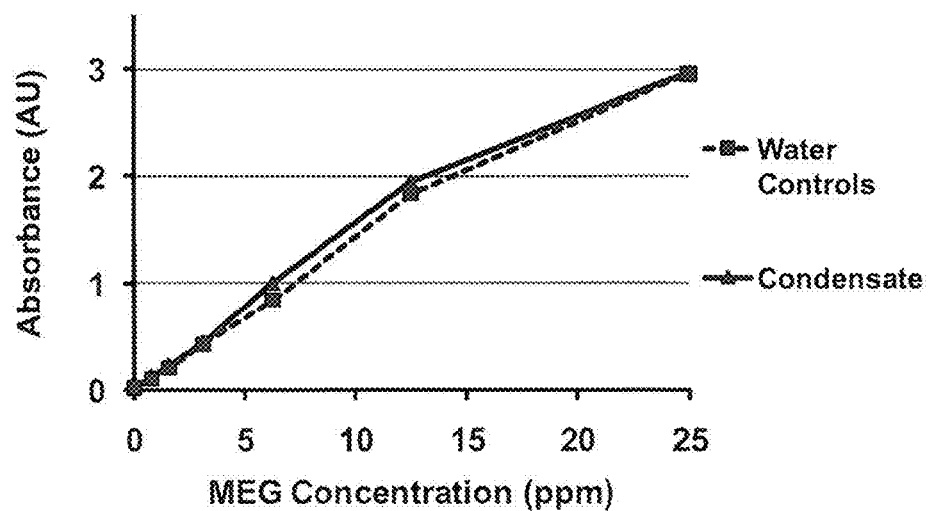
FIG. 5 is a graph showing the signal generated from a range of concentration of MEG in condensate, absorbance measured at maximum.
Figure 6:
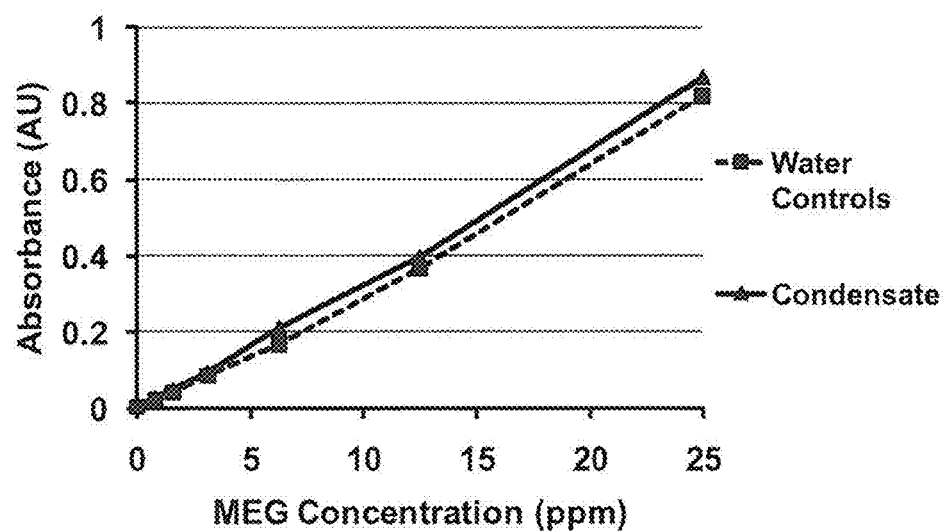
FIG. 6 is a graph showing the signal generated from a range of concentration of MEG in condensate, absorbance measured at suboptimal maximum.

Standard solutions were prepared to give a final concentration of MEG of 0, 0.78, 1.56, 3.1, 6.25, 12.5, 25, 50 and 100 ppm when 1 µl of the solution was added to 2 ml water. A solution of sodium metaperiodate in sodium acetate was also freshly prepared. 1 µl of the MEG solutions were added to 2 ml condensate, before adding 500 µl water, shaking, 500 µl of the periodate solution, and 1 mL of fluoral-P and heating. Following the incubation step the solution was placed in a cuvette and absorbance read. The results are shown in FIG. 5 and a clear increase in signal with increasing MEG concentration can be observed. As a number of the measurements are above 1, the samples were also analysed at suboptimal wavelength to determine if alternative wavelengths could be used for more concentrated samples. FIG. 6 shows this is possible. The absorbances measured during this experiment are all higher than those in experiments 1 and 2 since a modified method was used.

In the field, a sample may be taken from an oil or gas producing, refining, distilling or processing plant; from oil fields; from produced or overboard fluids; from fuels; from MEG reclamation or regeneration plants or from hydrocarbon streams. The samples may be taken in-line, at-line, on-line or offline. The reagents may be added to the sample by hand, or by automatic injector. The latter would offer the possibility for automating the system, which would make it especially reliable, simple and high-throughput.

Experiment 4: Testing Corrosion Inhibitor in Oil

Figure 7:
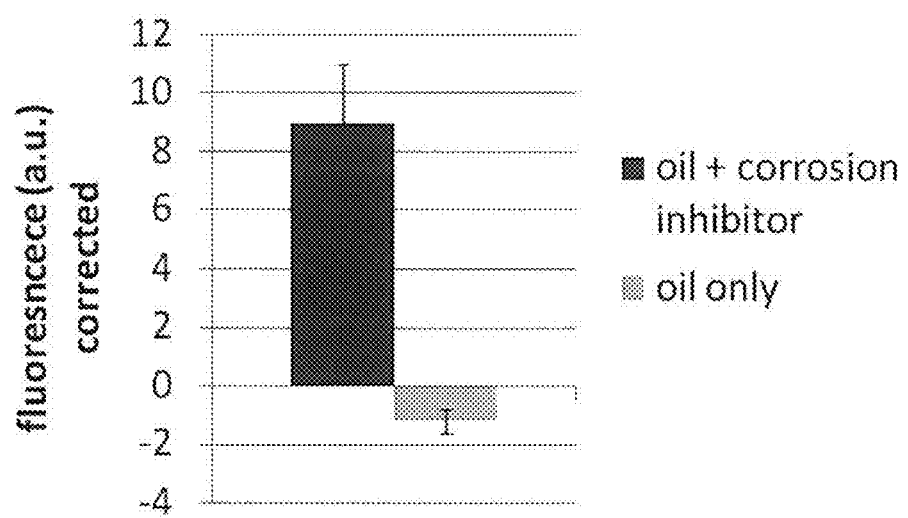
FIG. 7 is a graph showing signal generated from corrosion inhibitor in oil

To determine the presence of corrosion inhibitor in oil, a sample of oil to which a water dispersable corrosion inhibitor had, or had not, been added was tested. 5 uL of corrosion inhibitor was added to 5 mL of light condensate before being mixed vigorously by shaking. No corrosion inhibitor was added to a second 5 mL of condensate. 1 mL was transferred to a cuvette (in triplicate) before 2 mL of freshly made 60 nM Nile Red in water was added. The cuvette was inverted 10×, then left to stand for 30 seconds, to allow the phases to settle before being read on a handheld fluorometer with rhodamine filter sets. FIG. 7 shows an increased fluorescence signature from corrosion inhibitor-containing sample compared to the control.

Experiment 5: Measuring Ethanol Concentration

Figure 8:
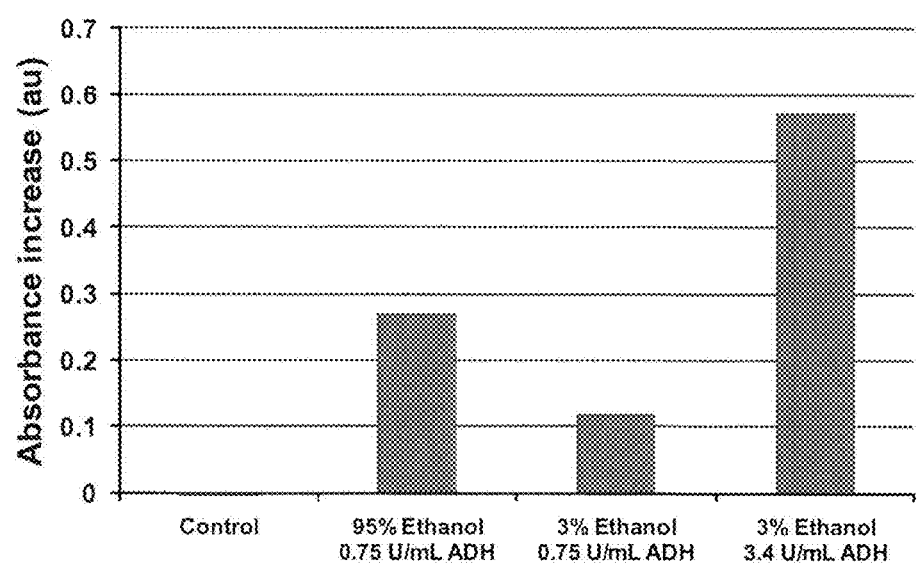
FIG. 8 is a graph showing signal generated from ethanol

The following method was used to measure ethanol concentration using alcohol dehydrogenase to generate a detectable product. 1.3 mL phosphate buffer (50 mM, pH 8,8), 0.1 mL aqueous ethanol solution, 1.5 mL $NAD^+$ (15 mM) and 0.1 mL alcohol dehydrogenase (ADH) containing 0.1% bovine serum albumin were added to a cuvette. A control was measured with the ADH omitted. The ethanol concentrations analysed were 95% and 3% and the ADH concentrations used were 0.75 U/mL and 3.4 U/mL. The absorbance at 340 nm was recorded. FIG. 8 shows the signal produced from different ethanol and enzyme concentrations.

Experimental 6: Testing Oil Samples with Detection Reagents

Figure 9:
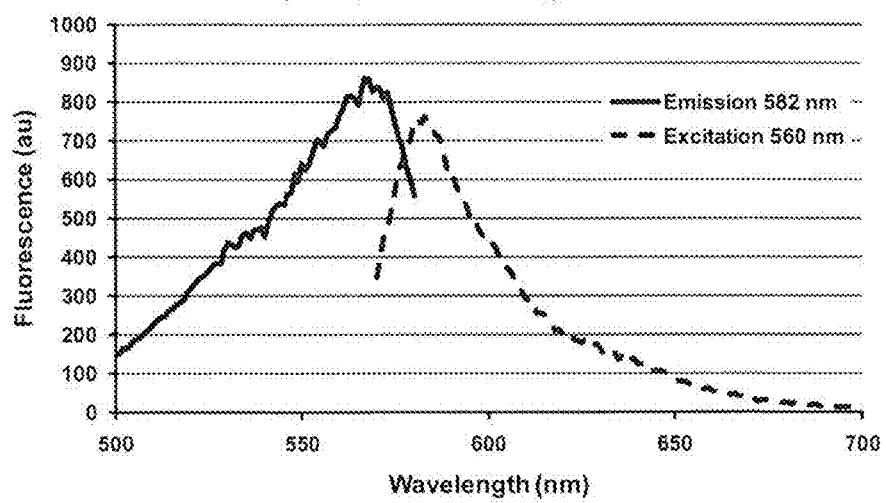
FIG. 9 is a graph showing signal generated from testing a number of reagents when used in the presence of methanol-containing oil
Figure 9:
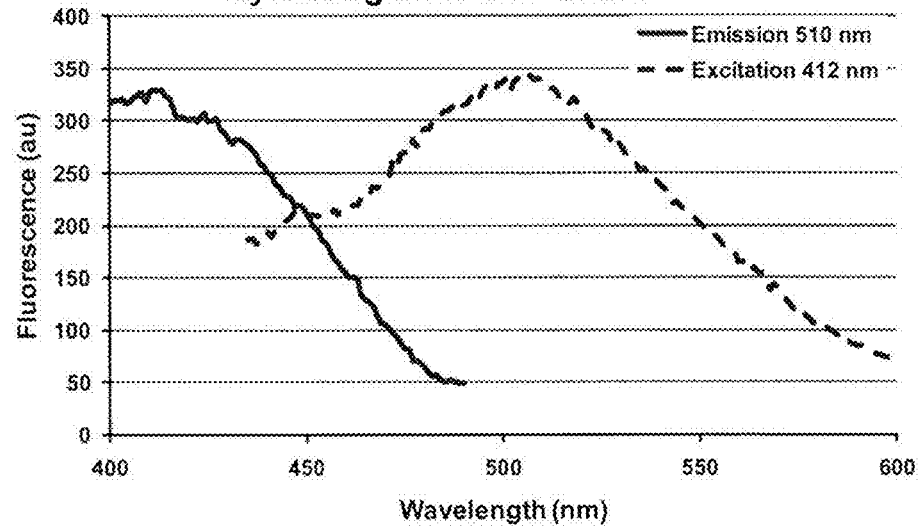

Treatment chemicals in oil samples are traditionally tested first by extracting them from oil, using water and then removing the aqueous layer with a separation step then adding detection reagents. This is because the oil can inactivate the detection reagents, opaque oil may scatter optical signals so introducing inaccuracies and reducing sensitivity, products of reactions can be solubilised back into the oil making them undetectable in the water layer and because where multiple reagents are used they may work under incompatible conditions such as temperature and pH so reducing sensitivity. Reactions with oil which contained methanol were set-up using four different sets of reagents, these were alcohol oxidase and amplex red, alcohol oxidase and MBTH (in presence of $FeCl_3$), alcohol dehydrogenase and $NAD^+$, alcohol dehydrogenase and Fluoral-P. All reactions were carried out in a single vial with the oil present. Two of the reactions gave signals, one gave a very low signal and one did not work. FIG. 9 shows the results for the successful reactions which used amplex red and ADH and Fluoral-P. The reaction with MBTH was unsuccessful and only a very low fluorescent signal was seen for ADH and $NAD^+$. It should be noted that the same reaction without oil present did work with MBTH indicating it is not clear or obvious that reactions which combine reagents and produced fluids in the same vial will work.

Experiment 7: Methanol in Crude Oil

Figure 10:
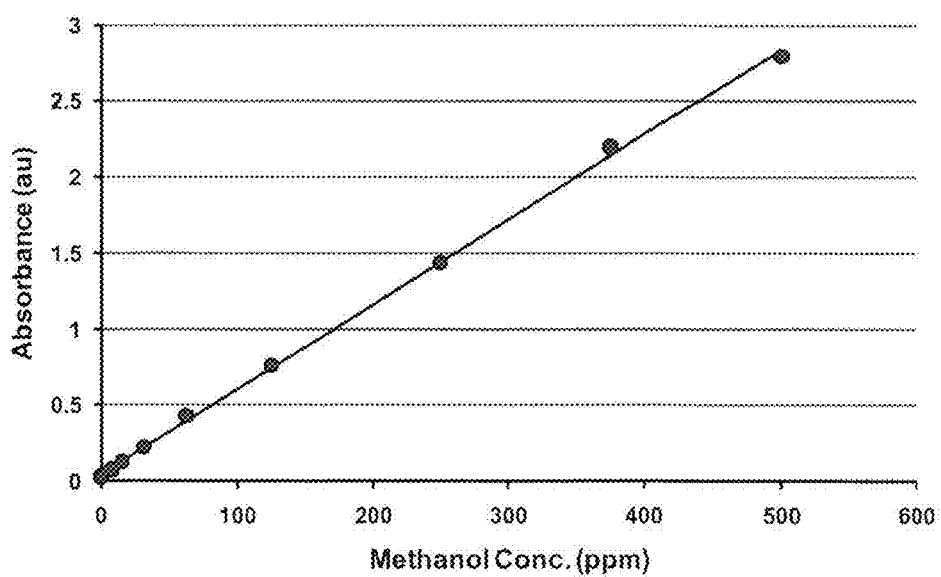
FIG. 10 is a graph showing that the signal generated can be proportional to the methanol concentration in produced fluids

For some applications it is important that methanol concentrations in produced fluids can be quantified. The following experiment demonstrates that the size of the signal generated can be proportional to the concentration of methanol present. Crude oil was spiked with methanol to final methanol concentrations of 500, 375, 250, 125, 62.5, 31.25, 15.6, 7.8 and 0 ppm. A portion was added to the aqueous reagents (alcohol oxidase, fluoral P with buffer) and heated and rotated end over end for 35 min, then the absorbance recorded. FIG. 10 shows the linear relationship between absorbance and methanol concentration.

Experiment 8: Methanol in Crude Oil and the Influence of Automation

To determine whether automation may reduce inter-user variability methanol-containing oil was mixed by hand (shaking) and with an automated end over end mixer. Methanol in dichloromethane was added to crude oil (final concentration 20 ppm). Water was added to extract the methanol from oil and the extraction was either achieved by shaking the sample manually (vigorously, or gently), or by automated mixing with heating in an adapted end over end mixer. The water phase was separated and detection reagents alcohol oxidase and fluoral P were added to the water extract and this mixture heated before absorbance was read.

Figure 11:
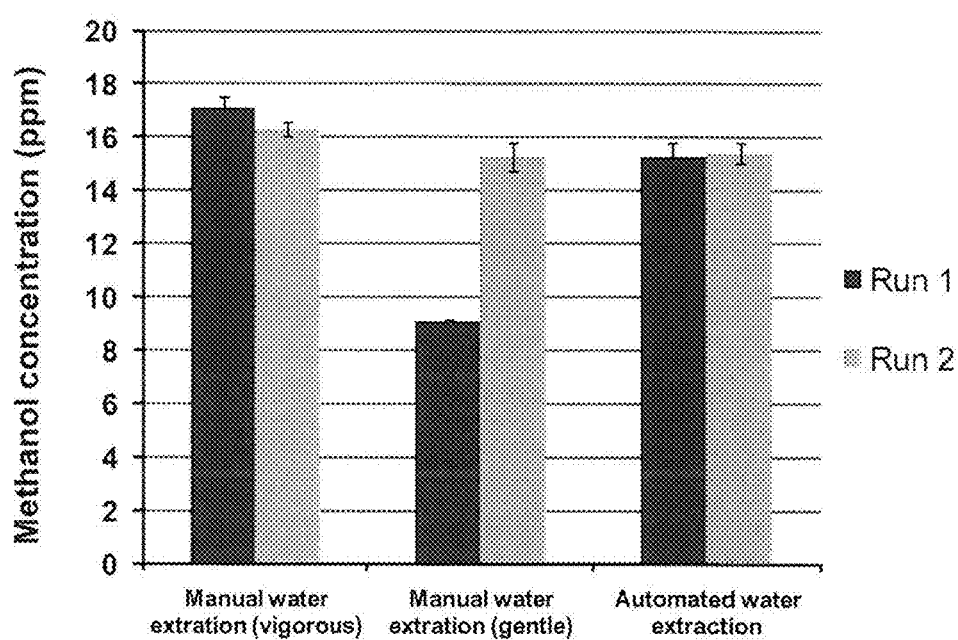
FIG. 11 is a graph showing benefits, in this case reduced variability, of using an automated mixing step

Absorbance readings were converted to methanol concentrations. FIG. 11 shows that differences were observed in manual methods (vigorous vs gentle) but that automation generated more consistent results.

Experiment 9: Extending the Range of the Methanol Assay

Figure 12:
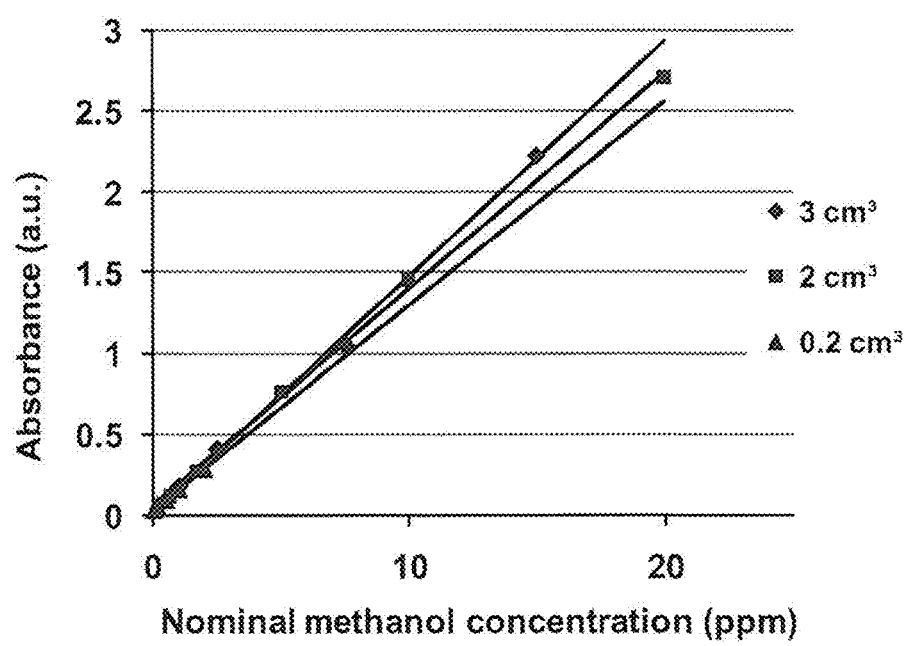
FIG. 12 is a graph showing how the range of the method may be extended by using reduced volumes of sample
Figure 13:
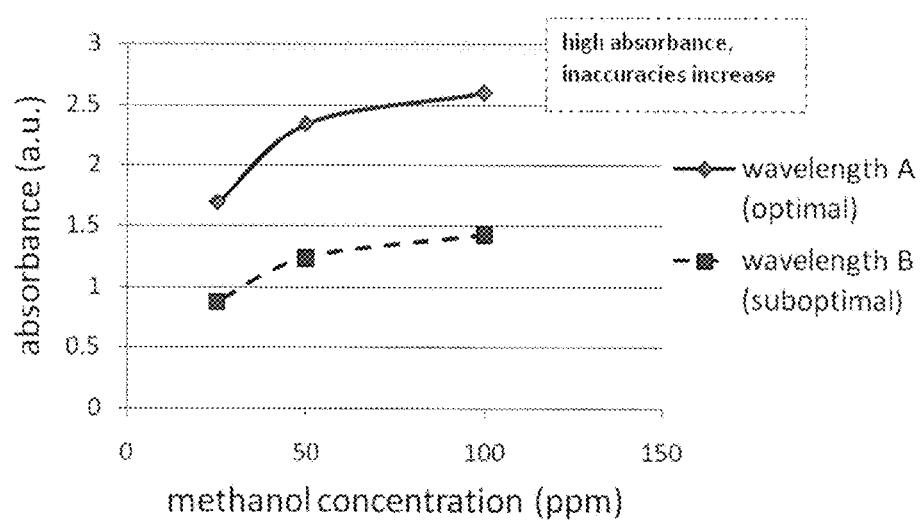
FIG. 13 is a graph showing how the range of the method may be extended at the higher end by using suboptimal conditions

The wider the dynamic range of any test the more applicable it is. Absorbance readings are only accurate up to 3 a.u. and given that the method disclosed here does not use a separation step dilution after extraction is not possible and any dilution is limited by the volume of the vial used, which is limited in turn by the dimensions of the detection equipment. Altering the volume of oil sample:detection reagent ratio allowed a range of concentrations to be quantified. FIG. 12 shown that the nominal methanol concentration does not vary greatly when using between 0.25 and 3 mL of oil sample, lines shown are linear trendlines. Altering the experimental conditions or detection wavelength to something suboptimal can extend the range to higher treatment chemical concentrations. FIG. 13 shows how signal from 100 ppm methanol in oil can be near the limit of detection (near 3 a.u.) under one set of conditions and markedly reduced under another.

We claim:

1. A method of monitoring water-soluble treatment chemicals in a fluid that is immiscible with water and which may or may not contain some aqueous fluid, where said water-soluble treatment chemical is a hydrate inhibitor, the method comprising:
   a. obtaining a sample of said fluid;
   b. adding a first reagent to the fluid sample, wherein the first reagent is an oxidising agent being reactive with the treatment chemical to produce a first product, wherein the first product is an aldehyde;
   c. adding a second reagent to the fluid sample, wherein the second reagent is an aldehyde reactive reagent being reactive with the first product in step (b) to produce an optically detectable second product wherein the second reagent is Fluoral P; and
   d. detecting an optically detectable product;
wherein the detection step takes place without separation of the aqueous phase containing the treatment chemicals from the fluid immiscible with water.

2. The method of claim 1, wherein the first and second reagent are added simultaneously.

3. The method of claim 1, wherein the first and second reagent are added sequentially.

4. The method according to claim 3, wherein the fluid immiscible in water is heated and/or mixed, rotated, vortexed, shaken, sonicated, inverted, filtered, or centrifuged after addition of the first reagent or a combination of these actions carried out simultaneously.

5. The method according to claim 1, wherein the second reagent is fluorogenic, chromogenic, luminescent, IR-active or Raman-active in the presence of the first product.

6. The method according to claim 1, wherein water is added to the fluid immiscible with water prior to step b.

7. The method according to claim 6, wherein the water added to the fluid immiscible in water in step (b) contains the first and second reagents.

8. The method according to claim 1, wherein water is added before or after reagents to make up the fluid immiscible in water to a specific volume.

9. The method according to claim 1, further comprising the step of pre-marking a container into which the fluid immiscible in water will be placed, in order to indicate desired volume.

10. The method according to claim 1, wherein the hydrate inhibitor comprises methanol, monoethylene glycol, or ethanol.

11. The method according to claim 1, wherein the first product is one of formaldehyde or acetaldehyde.

12. The method according to claim 1, wherein the first reagent is one of alcohol dehydrogenase, methanol dehydrogenase, alcohol oxidase, persulfate, permanganate, chromate, lead tetraacetate, periodate, periodic acid, boronic acid, glycerol dehydrogenase, monoethylene glycol dehydrogenase or ruthenium complexes such as $[Ru(III)(bpy)_3]^{3+}$.

13. The method according to claim 1, wherein the treatment chemical is methanol and the first reagent is alcohol oxidase.

14. The method according to claim 1, wherein the treatment chemical is monoethylene glycol and the first reagent is periodate.

15. The method according to claim 1, wherein the fluid immiscible with water and reagents are mixed, rotated, vortexed, shaken, sonicated, inverted, filtered, heated or centrifuged or a combination of these actions carried out simultaneously.

16. The method according to claim 1, wherein the fluid immiscible with water is heated above ambient temperature for a period of time to accelerate the reaction.

17. The method according to claim 1, wherein a treatment of the fluid sample is used to remove interfering chemicals from the fluid immiscible with water.

18. The method according to claim 17, wherein the treatment step comprises desalting the fluid immiscible with water.

19. The method according to claim 17, wherein the fluid immiscible with water is passed through a desalting column to remove salts.

20. The method according to claim 17, wherein ethylenediaminetetraacetic acid (EDTA) or other ion chelator is added to the fluid immiscible in water either before or at the same time as the first reagent and/or second reagent.

21. The method according to claim 17, wherein catalase is added to the fluid immiscible in water either before or at the same time as the first reagent and or second reagent.

22. The method according to claim 1, wherein the signal is detected using fluorescence, chemiluminescence, colourimetry, IR, Raman or UV-visible spectroscopy.

23. The method according to claim 1, wherein the signal is detected using fluorescence detector, luminescence detector, Raman detector, optical microscope, CCD camera, photographic film, fibre-optic device, photometric detector, MEMS device, single photon detector, spectrophotometer, chromatography system or by eye.

24. The method according to claim 1, wherein at least one positive and/or negative control samples are used.

25. The method according to claim 24, wherein the negative control contains inactivated first and/or second reagents.

26. The method according to claim 24, wherein the negative control contains only the second reagent.

27. The method according to claim 24, wherein the value of any optically detected background signal from the negative control is subtracted from the optically detected value obtained from a sample of fluid immiscible with water being analysed.

28. The method according to claim 24, wherein the positive control is aqueous or fluid immiscible with water known to contain treatment chemical.

29. The method according to claim 24, wherein calibration samples are used in order to create a calibration curve for the purposes of quantification.

30. The method according to claim 24, wherein the positive control or calibration samples are used to identify and compensate for variations due to different reagent activities.

31. The method according to claim 1, wherein a calibration factor is used to account for variations due to the differing extraction efficiencies from different fluids immiscible with water.

32. The method according to claim 1, wherein the range of detection is extended by altering the ratio of the fluid immiscible with water sample and aqueous phase.

33. The method according to claim 32, wherein the ratio of the fluid immiscible with water sample and aqueous reagents is altered by changing volume of aqueous phase and/or fluid immiscible with water.

34. The method according to claim 33, wherein the ratio of fluid immiscible with water and detection reagents is altered by diluting the fluid immiscible with water or a second fluid immiscible with water which does not contain the treatment chemical prior to mixing with aqueous phase.

35. The method according to claim 34, wherein the second fluid immiscible with water is heptane, hexane, petroleum ether, octane or kerosene.

36. The method according to claim 1, wherein the range of detection is altered by changing the conditions to alter speed of reaction, yield or detectability.

37. The method according to claim 36, wherein the temperature or timings, the pH of reagents, or the detection method is altered.

38. The method according to claim 1, wherein the fluid immiscible in water is added to the first and/or second reagent.

39. The method of claim 1, wherein the fluid sample is a single or multiphase fluid.

40. The method of claim 1, wherein the addition is carried out under pressure.

41. The method of claim 1, wherein the addition is carried out by bubbling the fluid immiscible with water through water or an aqueous solution of one or more reagents.

42. The method according to claim 1, wherein the method or steps within the method are automated.

43. A kit for monitoring of water-soluble treatment chemicals in a fluid that is immiscible with water according to claim 1.

* * * * *